United States Patent [19]

Vanlerberghe et al.

[11] Patent Number: 4,515,775

[45] Date of Patent: May 7, 1985

[54] POLYHYDROXYL NON-IONIC SURFACTANT, PROCESS FOR PREPARING THE SAME AND COSMETIC COMPOSITION CONTAINING THE SAME

[75] Inventors: Guy Vanlerberghe, Montjay-la-Tour; Henri Sebag, Paris, both of France

[73] Assignee: Societe Anonyme dite: L'Oreal, Paris, France

[21] Appl. No.: 68,390

[22] Filed: Aug. 21, 1979

Related U.S. Application Data

[60] Continuation of Ser. No. 796,232, May 12, 1977, abandoned, which is a division of Ser. No. 629,904, Nov. 7, 1975, abandoned, which is a continuation-in-part of Ser. No. 307,524, Nov. 17, 1972, abandoned.

[30] Foreign Application Priority Data

Nov. 18, 1971 [LU] Luxembourg .............................. 64289

[51] Int. Cl.³ ................................................ A61K 7/06
[52] U.S. Cl. ...................................... 424/70; 514/941; 514/560; 514/474
[58] Field of Search .................... 8/10.1, 10.2; 424/70, 424/170, 319, 307, 343, 320

[56] References Cited

U.S. PATENT DOCUMENTS

| | | | |
|---|---|---|---|
| 1,922,459 | 8/1933 | Schmidt et al. | 260/615 B |
| 2,089,569 | 8/1937 | Orthner et al. | 260/615 R |
| 2,327,053 | 8/1943 | Marple et al. | 260/615 R |
| 3,278,555 | 10/1966 | Ward | 260/615 B |
| 3,380,925 | 4/1968 | Blaser et al. | 260/615 B |
| 3,427,248 | 2/1969 | Lamberti et al. | 260/615 R |
| 3,674,902 | 7/1972 | Kalopissis et al. | 8/10.2 |
| 3,708,364 | 1/1973 | Kalopissis et al. | 252/156 |
| 3,719,636 | 3/1973 | Woftowicz et al. | 266/615 B |
| 3,865,542 | 2/1975 | Kalopissis et al. | 8/10.1 |
| 4,001,141 | 1/1977 | Kalopissis et al. | 8/10.1 |

*Primary Examiner*—Ethel G. Love
*Attorney, Agent, or Firm*—Cushman, Darby & Cushman

[57] ABSTRACT

Polyhydroxyl non-ionic surface active agents, for use in a cosmetic composition such as hair dye or shampoo composition is prepared by condensing glycidol on a polyhydroxyl fatty chain reactant in the presence of an acid catalyst at a temperature of 50°–120° C.

6 Claims, No Drawings

POLYHYDROXYL NON-IONIC SURFACTANT, PROCESS FOR PREPARING THE SAME AND COSMETIC COMPOSITION CONTAINING THE SAME

This application is a continuation of application Ser. No. 796,232, filed May 12, 1977, now abandoned which, in turn, is a division of application Ser. No. 629,904, filed Nov. 7, 1975, now abandoned, which, in turn, is a continuation of application Ser. No. 307,524, filed Nov. 17, 1972, now abandoned.

The present invention relates to a process for preparing a polyhydroxyl non-ionic surfactant by condensing glycidol on a mono- or polyhydroxyl fatty chain compound in the presence of an acid catalyst, to the resulting non-ionic surfactant and to a cosmetic composition containing said non-ionic surfactant.

The mono- or polyhydroxyl fatty chain compound usefully employed as an initial reactant in the process of this invention can be represented by the formula

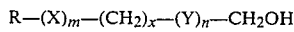

wherein X is selected from the group consisting of oxygen,

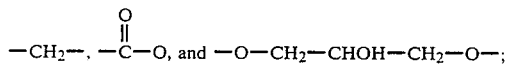

Y is selected from the group consisting of

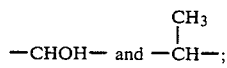

m, n and x each represent 0 or 1; and R represents a branched or linear, unsaturated or saturated hydrocarbon, preferably alkyl or alkenyle having from 6 to 18 carbon atoms or a mixture thereof.

Representative of said mono- or polyhydroxyl fatty chain compounds are linear fatty alcohols including 1-octanol, 1-decanol, 1-dodecanol, 1-tetradecanol, 1-hexadecanol; branched alcohols, for example, those having from 12 to 15 carbon atoms and sold by Shell under the name "Dobanols"; glycerol alkyl ethers corresponding to the above alcohols; products of condensation of 2-hydroxy glyceroloxy ethanol alkyl ethers; 1,2-alkanediols such as octanediol, decanediol, undecanediol, dodecanediol, tridecanediol, tetradecanediol, pentadecanediol, hexadecanediol, heptadecanediol and octadecanediol; glycerol esters of octanoic, decanoic, dodecanoic, tetradecanoic, hexadecanoic acid and octadecanoic acids the latter including oleic, stearic and isostearic acids. The various compounds listed above can be used alone or in admixture.

The acid catalysts that can be employed in the present invention are Lewis acids, particularly boron trifluoride, tin tetrachloride and antimony pentachloride.

In the presence of acid reaction catalysts and the absence of water, glycidol has a very strong tendency to polymerize, yielding polyglycerols that rapidly separate. Thus it is surprising that the present process makes it possible to obtain compounds soluble in water while employing relatively slight molar proportions of glycidol relative to said mono- or polyhydroxyl fatty chain compound.

By using 1 to 10 moles of glycidol per mole of said mono- or polyhydroxyl fatty chain compound, there results the non-ionic surface active agent of this invention which is dispersible or perfectly soluble in water with high cloud points.

The condensation reaction of this invention is carried out by slow addition of glycidol (the addition can last for several minutes to several hours and preferably from 30 minutes to 3 hours), to a mixture of the mono- or polyhydroxyl fatty chain compound, defined above, and the acid catalyst, at a temperature from 50° C. to 120° C.

Generally, 0.1 to 5 weight percent catalyst, relative to the reaction mass, is used. Addition of the catalyst can be made once or several times. Since these catalysts are very sensitive to water and base impurities, it is essential to eliminate any possible trace of these latter.

A mixture of compounds is formed for which the number of fixed hydroxypropylenoxy groups derived from the glycidol can be greater or less than the number of glycidol molecules used per molecule of the mono- or polyhydroxyl fatty chain compound. The various compounds of the mixture obtained can therefore comprise more or less long hydrophilic chains.

Further, the epoxy group of the glycidol can, at the time of condensation, be opened in two different ways and give rise either to two primary alcohol functions or to a primary alcohol function and a secondary alcohol function and the condensation reaction can be continued on any OH group present, various possibilities of condensation already existing at the start when the initial reactant is a polyhydroxyl fatty chain compound. Consequently, it is very difficult to represent the non-ionic surface active agent produced in accordance with the present invention by a formula.

Exothermicity of the reaction and thickening without the appearance of a second phase are two indicators of a correct evolution of the condensation reaction of this invention.

Another embodiment of the present invention relates to the non-ionic surfactants made in accordance with the process described above. For the most part, depending on the nature of radial R and the amount of glycidol used, the non-ionic surfactants are thick, colorless or slightly tinted oils or more or less hard, light colored pastes. With regard to their appearance, the non-ionic surfactants obtained by the process of this invention generally have a lighter color and are slightly more fluid than those obtained in the presence of an alkaline catalyst.

The surfactants of this invention can be employed as foaming agents, wetting agents, dispersing agents or emulsifiers and when used as emulsifiers they are more particularly employed in emulsifying oils in water.

The process of the present invention is particularly advantageous when the mono- or polyhydroxyl fatty chain initial reactant is a glycerol ester since it makes it possible essentially to obtain polyhydroxyl esters which do not contain more than one fatty chain per polyglycerol chain.

Actually the various known processes such as, for example, direct esterification of polyhydroxyl compounds or oxirane polyadditions in alkaline catalysis lead to statistical esterifications, i.e., the reaction mixture is made up, besides polyhydroxyl monoesters, of quite large amounts of di- or polyesters.

The present invention also relates to a cosmetic composition such as a shampoo composition, a hair dye composition, a dispersion or emulsion. These compositions are essentially characterized by the fact that they comprise an aqueous carrier and the surfactant prepared by the process of the present invention in amounts of about 0.1% to 80% by weight of the composition which has a pH between about 3 and 10.5.

The polyhydroxyl non-ionic surface active agent of the present invention can also be used to disperse alkaline earth soaps and in particular calcium and magnesium soaps. Therefore, these surface active agents can be used in compositions intended for foam baths thereby avoiding the annoying action of alkaline earth soaps. These compositions can contain from 5 to 80 weight percent of the non-ionic surface active agents prepared according to the process of the present invention and can have a pH between 5.5 and 8.

The shampoo compositions of the present invention generally contain 5 to 60 weight percent of the non-ionic surface active agents prepared in accordance with the present invention, said shampoo composition generally having a pH between 3 and 9.5.

The hair dye composition of the present invention contains, as a thickener or dye support, from 0.1 to 60 weight percent of the non-ionic surfactant prepared in accordance with the process of the present invention, the pH of these hair dye compositions being between 4 and 10.5.

The present invention also relates to a dispersion or emulsion and particularly to "oil in water" emulsion or dispersion.

The composition according to the present invention can be in the form of a liquid, cream, paste or gel and it can be packaged in a conventional aerosol bomb. Further, the composition according to the present invention can contain, besides a surfactant prepared according to the process of the present invention, other non-ionic surfactants as well as anionic, cationic, amphoteric and/or zwitterionic type surfactants. Further, the composition of the present invention can contain foam synergists, thickeners, pigments, dyes, perfumes, germicides, softeners, vegetable extracts and/or other adjuvants usually used in cosmetic compositions. The cosmetic composition of the present invention can also contain oxidation dyes or direct dyes and particularly anthraquinone, azo and/or nitro dyes of the benzene series type.

The invention will be illustrated by the following examples and unless otherwise specified all parts and percentages are by weight.

In this examples, the tin tetrachloride was used as 40% solution in $CCl_4$ and the boron trifluoride complex used contained 36% $BF_3$.

EXAMPLE 1

A mixture of compounds is obtained by condensing 4.6 moles of glycidol per mole of fatty alcohols of the formula $R-(X)_m-(CH_2)_n-(Y)_n-CH_2OH$ wherein R designates a mixture of alkyl radicals of $C_{12}$ and $C_{14}$ in a proportion of 70:30, and $m=x=n=0$, said fatty alcohols being made by Henkel International GmbH Dusseldorf (Germany) and marketed under the name "Dehydag".

To 19.8 g (0.1 mole) of fatty alcohols as defined above there are added at 105° C. 0.5 mole of tin tetrachloride ($SnCl_4$) in $CCl_4$, and then drop by drop, over a period of 1 hour 20 minutes, 34.5 g (0.46 mole) of glycidol.

About an hour after the start of addition of the glycidol, there is further added 0.2 ml of $SnCl_4/CCl_4$.

There is thus obtained a white product soluble in cold water, having a hydroxyl number of 605, a Kraft point (at 1% in water) of 15° C., a cloud point at 0.5% > 100° C. in demineralized water and in water containing 10% NaCl.

The foam heights measured with a Ross and Miles apparatus are, for concentrations of 0.5%, 0.2% and 0.05%, 19 cm, 16 cm and 10.5 cm, respectively.

The mixture of compounds obtained is a good dispersing agent for calcium soaps. Actually, under test conditions proposed by Alba Mendoza and Gomez Herera at the 5th International Detergents Congress in Barcelona in 1968, the minimum amount of surfactant necessary to disperse 50 mg of sodium oleate in 50 ml of water with a hardness corresponding to 400 ppm of calcium chloride, is between 5 and 10 mg.

EXAMPLE 2

A mixture of compounds is obtained by condensing 6 moles of glycidol per mole of fatty alcohol of the formula $R-(X)_m-(CH_2)_x-(Y)_n-CH_2OH$ wherein

$m=0$; $n=1$ when $x=0$ or $m=1$, $X=CH_2$, $n=0$ when $x=1$; R represents a mixture of alkyl radicals of $C_9H_{19}$, $C_{10}H_{21}$, $C_{11}H_{23}$ and $C_{12}H_{25}$ derived from alcohols marketed under the name "Dobanol 25" by the Shell Company. "Dobanol 25" is a mixture of primary alcohols of $C_{12}$-$C_{15}$, of which 14% is 2-methyl alkanols.

To 20.6 g (0.1 mole) of "Dobanol 25" as defined above heated under vacuum at 100° C. to eliminate any trace of moisture, there are added at this temperature 1 ml of SnCl catalyst in solution in carbon tetrachloride, and then over a period of 1½ hour, 44 g (0.6 mole) of glycidol. After about one hour from the start of addition there is further added 0.5 ml of the above catalyst. A white water soluble product is obtained, having a hydroxyl number of 577.

Foam heights measured with a Ross and Miles apparatus are, for concentrations of 0.5%, 0.2% and 0.05% 14.5 cm, 13 cm and 7.5 cm, respectively.

EXAMPLE 3

A mixture of compounds is obtained by condensing 4.5 moles of glycidol per mole of 1,2-hexadecanediol, where, in the formula $R-(X)_m-(CH_2)_x-(Y)_n-CH_2OH$, $m=x=0$, $Y=-CHOH-$, $n=1$ and $R=C_{14}H_{29}$.

The 1,2-hexadecanediol is available commercially or can be prepared by conventional hydroxylation of 1-hexadecene.

To 25.8 g (0.1 mole) of hexadecanediol heated to 65° C. there are added 0.12 ml of $BF_3$ acetic complex and then, drop by drop over a period of 1½ hours, 33.5 g (0.45 mole) of glycidol. A white water soluble product is obtained having a Kraft point of 38° C., a cloud point in demineralized water of >100° C., and a hydroxyl number: 607.

EXAMPLE 4

A mixture of compounds is obtained by polyaddition of 2.7 moles of glycidol per mole of reagent of the formula $R-(X)_m-(CH_2)_x-(Y)_n-CH_2OH$, wherein $m = 0$, $x = 1$, $Y = $ —CHOH—, $n = 1$ and R is a mixture of hydrocarbon radicals of $C_9H_{19}$ and $C_{11}H_{23}$ in the proportions of 55:45. This reagent is prepared by hydroxylation of a corresponding mixture of α-olefins, according to the process described by Swern in Organic Reactions Vol. VII, page 399.

To 1070 g (5 moles) of this reagent there are added 5.3 ml of boron trifluoride acetic complex at a temperature of 60° C., and then over a 2 hour period, drop by drop, at a temperature below 75° C., 1053 g (13.5 moles) of glycidol. The reaction is exothermic during the entire addition period.

The product obtained, which in the form of a very thick oil, tinted slightly light yellow, is water soluble, and has a hydroxyl number of 599.

The cloud point measured at a concentration of 0.5% is greater than 100° C. in demineralized water and in water containing 10% NaCl. Its Kraft point measured at a concentration of 1% is less than 0° C.

The product thus obtained is an excellent foaming agent and foam heights measured with a Ross and Miles apparatus, at concentrations of 0.5%, 0.2% and 0.05% are respectively, 20 cm, 19.5 cm and 13 cm.

Tested on a rabbit in a 4% concentration (0.1 molar solution), this product shows absolutely no agressiveness toward the eye, which is very important for its use in shampoos.

The mixture of compounds thus obtained is also a good dispersing agent of calcium soaps.

Under the test conditions proposed by Alba Mendoza and Gomez Herera at the 5th International Detergents Congress in Barcelona in 1968, the minimum amount of compounds necessary to disperse 50 mg of sodium oleate in 50 ml of water with a hardness corresponding to a content of 400 ppm of calcium chloride is between 5 and 10 mg, which makes it possible to classify it as a good dispersing agent.

This property, added to the preceding ones, makes it possible to use it in foam bath compositions.

EXAMPLE 5

A mixture of compounds is obtained by condensing 2.7 moles of glycidol per mole of reagent of the formula $R—(X)_m—(CH_2)_x—(Y)_n—CH_2OH$ wherein $m = 0$, $x = 1$, $n = 1$, $Y = $ —CHOH— and R is a mixture of hydrocarbon radicals of $C_8H_{17}$, $C_9H_{19}$, $C_{10}H_{21}$ and $C_{11}H_{23}$. This reagent is a mixture of α-diols marketed by the Archer Daniels Midland Company, Minneapolis, Minnesota, under the name "ADOL 114".

To 21 g (0.1 mole) of Adol 114, as defined above, there are added at 65° C. 0.1 ml of $BF_3$ acetic complex, and then drop by drop over a period of 1½ hours, 20.8 g (0.27 mole) of glycidol.

The resulting product, which is very slightly tinted a light yellow, is water soluble. It also exhibits cloud points in demineralized water and in water containing 10% NaCl of 69° and 67° C., respectively. Further, it produces foam heights measured with a Ross and Miles apparatus for concentrations of 0.5%, 0.2% and 0.05%, of 20 cm, 20 cm and 11.5 cm, respectively. Its hydroxyl number is 622.

EXAMPLE 6

A mixture of compounds is obtained by condensing 4 moles of glycidol per mole of reagent of the formula $R—(X)_m—(CH_2)_x—(Y)_n—CH_2OH$ wherein $m = x = 0$, $n = 1$, $Y = $ —CHOH— and R is a mixture of alkyl radicals of $C_{13}$ to $C_{16}$. This reagent is a mixture of α-diols of $C_{15}$–$C_{18}$ marketed by the Archer Daniels Midland Company, Minneapolis, Minnesota under the name "Adol 158".

To 26 g (0.1 mole) of "Adol 158", as defined above, there are added at 65° C. over a period of 1½ hours 0.12 ml of $BF_3$ acetic complex and then 30 g (0.4 mole) of glycidol.

The resulting product which is very slightly tinted yellow, dissolves in water and presents a slight cloud. Its hydroxyl number is 526.

EXAMPLE 7

A mixture of compounds is obtained by condensing 4 moles of glycidol per mole of glycerol tetradecylether of the formula $R—(X)_m—(CH_2)_x—(Y)_n—CH_2OH$ wherein $X = 0$, $Y = $ —CHOH—, $m = x = n = 1$, and $R = C_{14}H_{29}$.

To 11.5 g (0.04 mole) of distilled glycerol tetradecylether there are added at a temperature of 65° C., 0.05 ml of $BF_3$ acetic complex and then 12 g (0.16 mole) of glycidol.

A white water soluble product is obtained, whose Kraft point measured at a concentration of 1% is 26° C.

Cloud points of this surfactant in a 0.5% solution in demineralized water and in water containing 10% NaCl are greater than 100° C. Its hydroxyl number: 588.

EXAMPLE 8

A mixture of compounds is obtained by condensing 2.5 moles of glycidol on one mole of reagent of the formula $R—(X)_m—(CH_2)_x—(Y)_n—CH_2OH$ wherein X is

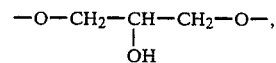

$m = x = 1$, $n = 0$ and R is $C_{12}H_{25}$.

To 9 g (0.029 mole) of this dihydroxyl reagent there are added at 70° C., 0.04 ml of $BF_3$ acetic complex, and then at a temperature between 70 and 75° C., over a 30 minute period, 5.2 g (0.07 mole) of glycidol.

The product obtained is perfectly water soluble. Its cloud point at 0.5% in demineralized water is 88° C., and in water containing 10% NaCl, it is 45° C. Its Kraft point is <0° C. and its hydroxyl number is 487.

EXAMPLE 9

A mixture of compounds is obtained by condensing 2.5 moles of glycidol per mole of glycerol monolaurate of the formula $R—(X)_m—(CH_2)_x—(Y)_n—CH_2OH$ wherein

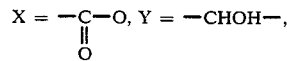

$m = x = n = 1$ and $R = C_{12}H_{25}$.

The glycerol monolaurate is prepared by condensing 34 g (0.46 mole) of glycidol on 79 g of lauric acid in the presence of 1 g of sodium methylate in methanol solution (4.5 meq/g) milliequivalent/gram) at a temperature of 115°–120° C. for 3 hours. The reaction is practically quantitative. 0.5 ml of concentrated hydrochloric acid is added to neutralize the catalyst completely and the glycerol monolaurate is separated by molecular distillation.

To 18 g (0.066 mole) of ester thus obtained, there are added at 100° C. 0.3 ml of SnCl₄ in solution in carbon tetrachloride, and then at a temperature between 100° and 110° C., over a 1 hour period, 12.2 g (0.165 mole) of glycidol.

The white product thus obtained dissolves in water with thickening of the solution and it presents a slight opalescence.

EXAMPLE 10

A mixture of compounds is obtained by condensing 5 moles of glycidol per mole of glycerol stearate of the formula R—(X)$_m$—(CH$_2$)$_x$—(Y)$_n$—CH$_2$OH wherein

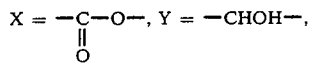

m=x=n=1 and R=alkyl C₁₇H₃₅.

Glycerol stearate is marketed under the name "Tegin 90" by the Goldschmidt Chemical Division of Wilson Pharmaceutical and Chemical Corp., New York.

To 52.5 g (0.15 mole) of "Tegin 90" as defined above, there are added at 100° C. 1 ml of SnCl₄ in solution in carbon tetrachloride, and then at a temperature between 100° C. and 110° C., over a 1 hour and 45 minute period, 55.5 g (0.75 mole) of glycidol.

A white product is thus obtained which dissolves in water and produces a slight cloud. Its hydroxyl number is 543.

EXAMPLE 11

The method outlined in Example 10 is repeated using, however 17.5 g (0.05 mole) of "Tegin 90", 0.7 ml of catalyst and 26 g (0.35 mole) of glycidol.

A white water soluble product is obtained having a Kraft point of 39° C., a cloud point >100° C. and a hydroxyl number of 593.

Under the tests conditions of dispersion of calcium soaps, used in Examples 1 and 4, the minimum amount of mixture of compounds necessary to disperse 50 mg of sodium oleate is between 5 and 10 mg.

EXAMPLE 12

A mixture of compounds is obtained by condensing 9 moles of glycidol to 1 mole of glycerol oleate of the formula R—(X)$_m$—(CH$_2$)$_x$—(Y)$_n$—CH$_2$OH wherein

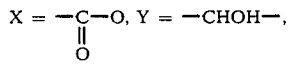

m=x=n=1 and R represents the hydrocarbon radical of oleic acid.

The glycerol oleate used is obtained by heating 46.5 g (0.170 mole) of oleic acid, 20 g (0.27 mole) of glycidol and 5 g of sodium chloride in 250 g of water. The product thus prepared has a free acid number of 0.27 meq/g (milliequivalent/gram).

To 13 g (0.038 mole) of this ester there are added at a temperature of 95° C., 0.8 ml of SnCl₄ in carbon tetrachloride and then drop by drop over a period of 1 hour 40 minutes, 25 g (0.34 mole) of glycidol.

During addition of the glycidol, there are further added, in 2 fractions, 0.7 ml of catalyst.

The product obtained is in the form of a translucent paste of soft consistency which dissolves in water with a very slight opalescence. Its hydroxyl number: 616.

EXAMPLE 13

A mixture of compounds is obtained by condensing 9 moles of glycidol per mole of glycerol isostearate of the formula R—(X)$_m$—(CH$_2$)$_x$—(Y)$_n$—CH$_2$OH wherein

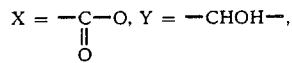

m=x=n=1 and R represents the hydrocarbon radical of isostearic acid.

To 19.5 g (0.05 mole) of glycerol isostearate prepared in a manner essentially the same as that utilized for the preparation of glycerol oleate as outlined in Example 12, there are added over a 2 hour period, at a temperature of 95° C., 0.4 ml of SnCl₄ in carbon tetrachloride and then drop by drop 34 g (0.45 mole) of glycidol. During the reaction there is further added, in 3 fractions, 0.12 ml of catalyst.

The product obtained is in the form of a translucent paste of soft consistency which dissolves in water with a very slight cloud. Its hydroxyl number: 532.

The commercially available fatty alcohols used in the above Examples are more specifically identified as follows:

Dobanol 25: carbon number range —C₁₂—C₁₅; Odor-mild; melting range, °C—21 to 23; color, APHA (Pt-Co) - 20; specific gravity, 25°/25° C.—0.834; viscosity, cs at 100° F.—15; flash point (PMCC) °F—285; boiling range (ASTM D-1078), °C.—1BP, 270—EP, 293; hydroxyl value, eq/100 g—0.483; average molecular weight (from hydroxyl value)—207; water (Karl Fischer), % w.—0.07; acid value, eq/100g —less than 0.001; saponification value, eq/100 g—0.001; carbonyl value, ppm as CO-80; iodine number, g I₂/100 g—0.2 and sulphatability (chlorosulphonic acid), %—98.7; carbon distribution, % wt—C₁₂—20; C₁₃—33, C₁₄—29 and C₁₅—18;

Adol 114: iodine value—2.7; acid value—0.08; saponification value—1.2; hydroxyl value—520; color—25 APHA; closed tube melting point—46° C.; viscosity at 100° C.—0.3 stokes; specific gravity 60°/25° C.—0.8870; flash point, Cleveland Open Cup—160° C.; boiling point range—100° C.—189° C. at 5 mm Hg; and molecular weight distribution %—C₁₀—4.2, C₁₁—26.6, C₁₂—25.3, C₁₃—25.3, C₁₄—18.6 and C₁₅—trace;

Adol 158: iodine value—3.5; acid value—0.09; saponification value—2.0; hydroxy value—430; color—25 APHA; closed tube melting point—64° C.; viscosity at 100° C.—0.3 stokes; specific gravity 60°/25° C.—0.8695; flash point, Cleveland Open Cup—190° C.; boiling point range—144° C.—210° C. at 4 mm Hg; and molecular weight distribution, %—C₁₃—0.9; C₁₄—1.3; C₁₅—30.0, C₁₆—32.4, C₁₇—23.2 and C₁₈—12.2.

EXAMPLES OF USE

EXAMPLE 14

A very fine emulsion is prepared having the following composition:

| | |
|---|---|
| Mixture of compounds obtained according to Example No. 10 | 11% |
| Paraffin oil | 45% |
| Water | 44% |

The mixture of compounds according to Example 10 is dispersed in paraffin oil, and at a temperature of 75° C., water is added and it is allowed to cool with stirring. This "oil in water" type emulsion constitutes a beauty milk for hands.

EXAMPLE 15

A non-ionic shampoo composition having the following composition is prepared:

| | |
|---|---|
| Mixture of compounds obtained according to Example No. 4 | 8 g |
| Oxyethylened lanolin (sold under the name Atlas G 1741 by Atlas Chemical Industries, Wilmington, Delaware) | 5 g |
| Hydroxypropylmethyl cellulose | 0.4 g |
| Water sufficient for | 100 g |
| The pH is 7. | |

EXAMPLE 16

A cationic shampoo composition having the following composition is prepared:

| | |
|---|---|
| Mixture of compounds obtained according to Example 4 | 8 g |
| 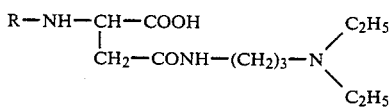 | 5 g |
| R = alkyl derived from copra fatty acids | |
| Hydroxymethylcellulose | 0.25 g |
| Lactic acid, q.s.p. pH 4 | |
| Water, q.s.p. | 100 g |

EXAMPLE 17

A cationic shampoo having the following composition is prepared:

| | |
|---|---|
| Mixture of compounds prepared according to Example 5 | 6 g |
|  | 12 g |
| 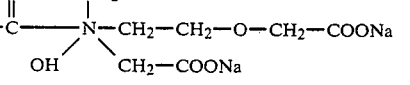, wherein R = lauryl | 5 g |
| Lactic acid, q.s.p. pH 6 | |
| Water, q.s.p. | 100 g |

EXAMPLE 18

The following composition intended for a foam bath is prepared:

| | |
|---|---|
| Mixture of compounds prepared according to Example 4 | 15 g |
| Mixture of dodecanediol:tetradecanediol 50:50 | 2 g |
| Triethanolamine myristylether sulfate | 20 g |
| Lauryl diethanolamide | 5 g |
| Lactic acid, q.s.p. pH 6 | |
| Water, q.s.p. | 100 g |

What is claimed is:

1. A shampoo composition comprising an aqueous carrier and a water-soluble polyhydroxyl non-ionic surfactant prepared by condensing at a temperature of 50°-120° C. glycidol and a hydroxy fatty chain reactant in a condensation reaction mixture consisting essentially of an acid catalyst selected from the group consisting of boron trifluoride and tin tetrachloride, glycidol and a hydroxy fatty chain reactant having the formula $R-CH_2-CHOH-CH_2OH$ wherein R is a 55:45 mixture of $C_9H_{19}$ and $C_{11}H_{23}$, the molar ratio of glycidol to said hydroxy fatty chain reactant being 2.7:1, said surfactant being present in an amount of about 5-60 percent by weight of said composition and said composition having a pH ranging from about 3 to 9.5.

2. The shampoo composition of claim 1 which also includes a compound of the formula

wherein R is alkyl derived from copra fatty acids.

3. A foam bath composition comprising an aqueous carrier and a water-soluble polyhydroxyl non-ionic surfactant prepared by condensing at a temperature of 50°-120° C. glycidol and a hydroxy fatty chain reactant in a condensation reaction mixture consisting essentially of an acid catalyst selected from the group consisting of boron trifluoride and tin tetrachloride, glycidol and a hydroxy fatty chain reactant having the formula $R-CH_2-CHOH-CH_2OH$ wherein R is a 55:45 mixture of $C_9H_{19}$ and $C_{11}H_{23}$, the molar ratio of glycidol to said hydroxy fatty chain reactant being 2.7:1, said surfactant being present in an amount of about 5-80 percent by weight of said composition and said composition having a pH from about 5.5 to 8.

4. The foam bath composition of claim 3 which also includes a 50:50 mixture of dodecanol and tetradecanol, triethanolamine myristyl ether sulfate and lauryl diethanolamide.

5. A beauty milk composition consisting of an oil-in-water emulsion comprising an oil phase, a water phase and water-soluble polyhydroxyl non-ionic surfactant prepared by condensing at a temperature of 50°-120° C. glycidol and a hydroxy fatty chain reactant in a condensation reaction mixture consisting essentially of an acid catalyst selected from the group consisting of boron trifluoride and tin tetrachloride, glycidol and a hydroxy fatty chain reactant having the formula $$C_{17}H_{35}-\overset{O}{\underset{\|}{C}}-O-CH_2CHOH-CH_2OH,$$

the molar ratio of glycidol to said hydroxy fatty chain reactant being 5:1, said surfactant being present in an amount of about 0.1-80 percent by weight of said composition so as to form said emulsion and said composition having a pH ranging from about 3 to 10.5.

6. The beauty milk composition of claim 5 wherein the oil phase is paraffin oil.

* * * * *